(12) United States Patent
Auberger et al.

(10) Patent No.: US 12,653,700 B2
(45) Date of Patent: Jun. 16, 2026

(54) ORTHOPEDIC JOINT AND ORTHOPEDIC DEVICE

(71) Applicant: Otto Bock Healthcare Products GmbH, Vienna (AT)

(72) Inventors: Roland Auberger, Vienna (AT); Janos Kalmar, Vienna (AT); Juan Pablo Mejia Nino, Mödling (AT); Dominik Reiter, Steyr (AT)

(73) Assignee: OTTO BOCK HEALTHCARE PRODUCTS GMBH, Vienna (AT)

( * ) Notice: Subject to any disclaimer, the term of this patent is extended or adjusted under 35 U.S.C. 154(b) by 357 days.

(21) Appl. No.: 17/288,433

(22) PCT Filed: Oct. 14, 2019

(86) PCT No.: PCT/EP2019/077817
§ 371 (c)(1),
(2) Date: Apr. 23, 2021

(87) PCT Pub. No.: WO2020/083696
PCT Pub. Date: Apr. 30, 2020

(65) Prior Publication Data
US 2021/0236307 A1     Aug. 5, 2021

(30) Foreign Application Priority Data
Oct. 23, 2018     (DE) ..................... 10 2018 126 324.4

(51) Int. Cl.
*A61F 2/70*          (2006.01)
*A61F 2/60*          (2006.01)
(Continued)

(52) U.S. Cl.
CPC ............... *A61F 2/70* (2013.01); *A61F 2/604* (2013.01); *A61F 2/64* (2013.01); *A61F 5/0123* (2013.01);
(Continued)

(58) Field of Classification Search
None
See application file for complete search history.

(56) References Cited

U.S. PATENT DOCUMENTS

| | | | |
|---|---|---|---|
| 2,646,793 | A | 7/1953 | Swiech et al. |
| 2007/0038168 | A1 | 2/2007 | Turrini et al. |
| | | (Continued) | |

FOREIGN PATENT DOCUMENTS

| | | |
|---|---|---|
| CN | 1280476 A | 1/2001 |
| CN | 104940004 A | 9/2015 |
| | (Continued) | |

OTHER PUBLICATIONS

PCT/EP2019/077817 International Search Report dated Feb. 7, 2020.

(Continued)

*Primary Examiner* — David H Willse
(74) *Attorney, Agent, or Firm* — HOLLAND & HART LLP

(57) ABSTRACT

The invention relates to an orthopedic joint with a first component, a second component that is arranged on the first component such that it can be swiveled about a swivel axis, and at least one damper that is configured and arranged to damp a swiveling of the first component relative to the second component, and an actuator for swiveling the first component relative to the second component in at least one direction. According to the invention, the actuator is arranged on the first component or the second component on a medial or lateral side such that it can be detached.

13 Claims, 2 Drawing Sheets

(51) Int. Cl.

| | |
|---|---|
| *A61F 2/64* | (2006.01) |
| *A61F 5/01* | (2006.01) |
| *B25J 9/00* | (2006.01) |
| *A61F 2/50* | (2006.01) |
| *A61F 2/68* | (2006.01) |

(52) U.S. Cl.

CPC .......... *A61F 5/0125* (2013.01); *B25J 9/0006* (2013.01); *A61F 2002/5006* (2013.01); *A61F 2002/5038* (2013.01); *A61F 2002/5083* (2013.01); *A61F 2002/5089* (2013.01); *A61F 2002/6854* (2013.01); *A61F 2002/701* (2013.01); *A61F 2002/704* (2013.01); *A61F 2005/0155* (2013.01); *A61F 2005/0158* (2013.01); *A61F 2005/0169* (2013.01); *A61F 2005/0179* (2013.01); *A61H 2201/1215* (2013.01)

(56) References Cited

U.S. PATENT DOCUMENTS

| | | | |
|---|---|---|---|
| 2010/0198362 | A1 | 8/2010 | Puchhammer |
| 2010/0298746 | A1 | 11/2010 | Shimizu et al. |
| 2011/0009788 | A1 | 1/2011 | Kelly et al. |

| | | | | | |
|---|---|---|---|---|---|
| 2015/0051528 | A1 | | 2/2015 | Gilbert et al. | |
| 2015/0173929 | A1 | | 6/2015 | Kazerooni et al. | |
| 2016/0158029 | A1 | * | 6/2016 | Kuiken ..................... | A61F 2/64 623/24 |
| 2017/0049659 | A1 | * | 2/2017 | Farris ..................... | B25J 9/1045 |
| 2018/0110632 | A1 | | 4/2018 | Errico et al. | |

FOREIGN PATENT DOCUMENTS

| | | | | | | |
|---|---|---|---|---|---|---|
| CN | 107854813 | A | * | 3/2018 | ........... | A61H 1/0274 |
| CN | 108135721 | A | | 6/2018 | | |
| JP | 2016174681 | A | | 10/2016 | | |
| KR | 100688327 | B1 | | 3/2007 | | |
| KR | 10-1514245 | B1 | * | 4/2015 | ......... | B25J 17/0241 |
| WO | 2010064063 | A1 | | 6/2010 | | |
| WO | 2011057793 | A1 | | 5/2011 | | |

OTHER PUBLICATIONS

China Patent Office "Search Report", issued in connection with China Patent Application No. 201980069469.1 dated Jan. 26, 2024 (2 pages).

China Patent Office "Decision to Grant", issued in connection with China Patent Application No. 201980069469.1 dated Sep. 3, 2024 (4 pages of English Translation and 4 pages Original Document).

* cited by examiner

ORTHOPEDIC JOINT AND ORTHOPEDIC DEVICE

CROSS REFERENCE TO RELATED APPLICATIONS

This application is a U.S. National Entry and claims priority to PCT International Patent Application No. PCT/EP2019/077817 filed 14 Oct. 2019, and entitled ORTHO-PAEDIC JOINT AND ORTHOPAEDIC DEVICE," which claims priority to German Patent Application No. 10 2018 126 324.4 filed 23 Oct. 2018, the entire disclosures of which are incorporated herein by this reference.

BACKGROUND

The invention relates to an orthopedic joint with a first component, a second component arranged on the first component such that it can be swivelled about a swivel axis, and an actuator for swivelling the first component relative to the second component in at least one direction. The invention also relates to an orthopedic device with at least one such joint.

An orthopedic joint is known from WO 2016/094413 A1, for example.

Orthopedic joints, such as prosthetic knee joints, have been known from the prior art for many years and are offered in a wide variety of embodiments. So-called passive orthopedic joints do not have their own drive, but only a damper with which a swivel movement of the two components relative to one another can be damped. The damper makes it possible to achieve a more or less natural gait pattern in the wearer of a prosthesis with such a knee joint. Modern passive orthopedic joints can be designed in such a way that the damping is adjustable. For example, a throttle valve in a hydraulic circuit can be opened or closed to decrease or increase a damping generated by a hydraulic damper. In order to achieve this at the right time, for example in a gait cycle, the orthopedic joint can have at least one sensor, the measurement values of which are evaluated by an electronic data processing device, which assumes the task of an electronic control unit, and used to control the damper. Although such joints often require their own power supply, they are passive orthopedic devices. However, a damper is not absolutely necessary even with passive orthopedic joints. There are also passive joints which work without dampers, so that the two components can oscillate freely.

Active orthopedic joints feature their own actuator, for example in the form of an electric motor or a pump, by which an orthopedic joint can be actively actuated, i.e. by actuating the actuator the first component can be swivelled relative to the second component about the swivel axis. Alternatively or additionally, the actuator can also counteract swivelling as a damper, which is advantageous, for example, in an artificial knee joint when walking downhill.

However, the ability to actively move an orthopedic joint is often only necessary or advantageous for the user in certain movement situations, stages of therapy or training conditions. It has been proven to be advantageous if the actuator can be switched on and off. The actuator can therefore be brought into an active state in which it is configured to swivel the first component relative to the second component in at least one direction. However, the actuator can also be brought into a passive state in which it has no influence on the movement of the orthopedic joint, so that the active orthopedic joint becomes a passive orthopedic joint in this state of the actuator.

However, a disadvantage of such joints of the prior art is that the actuator entails an increased weight and is also arranged on the lower leg, so that an increased torque is also required to swivel the first component relative to the second component about the swivel axis. The entire orthopedic joint is structurally complex and therefore costly and also heavy.

SUMMARY

The invention aims to eliminate or at least mitigate the disadvantages of the prior art.

The invention solves the task by way of an orthopedic joint, which is characterized in that the actuator is arranged on the first component and/or the second component on a medial or lateral side such that it can be detached.

This configuration achieves several advantages. Due to the detachable arrangement of the actuator, it can be easily removed if the actuator is not to be used, so that the resulting passive orthopedic joint does not have any additional weight caused by the actuator that is not required. In addition, due to the arrangement medially or laterally to the joint, i.e. shifted along the swivel axis, no additional torque or moment of inertia is generated when the first component is swivelled relative to the second component about the swivel axis. It is especially advantageous if the actuator can be fixed on both the medial and the lateral side. This is advantageous, for example, when the orthopedic joint is used as a knee joint, as both a right knee joint and a left knee joint can be equipped with the same actuator. A passive knee joint is preferably designed to be symmetrical to a sagittal plane and features corresponding coupling means on both the medial and lateral sides with which the drive can be connected. This greatly reduces the number of coupling adapters or actuator housings or actuators required.

In addition, the configuration according to the invention renders it possible to arrange different actuators, which may differ in their motor capacity for example, on the first component or the second component. In this way, for example, training progress can be taken into account. Over time, for example, the motor power required by a patient with an active orthopedic joint may decrease, for example, with training successes. With the configuration of the orthopedic joint according to the invention, an actuator can be easily removed from the first component or the second component and replaced with a different actuator with a lower or, if necessary, higher motor output. This is advantageous, for example, when a wearer of a prosthesis in whose prosthesis at least one orthopedic joint according to the invention is used wants to swim or bathe. In this case, the actuator, which may contain an electric motor for example, can be easily dismantled from the first component or the second component and the orthopedic joint used in water as a passive orthopedic joint.

The orthopedic joint preferably has at least one damper that is configured and arranged to damp a swivelling of the first component relative to the second component. The damping caused by the damper is preferably adjustable. It is especially preferable if the damping can be adjusted during the swivelling of the first component relative to the second component.

In a preferred configuration, a drive shaft of the actuator extends parallel to the swivel axis. It is especially preferable if the drive shaft extends coaxially to the swivel axis. This allows the actuator to be arranged at the side, i.e. medially or laterally, next to the first component and/or the second component through which the swivel axis passes. The swivel axis is not necessarily a separate component. It can also be designed as a theoretical swivel axis about which a swivelling of the first component relative to the second component occurs. By arranging the actuator along this swivel axis, the additional torque caused by the weight of the drive that has to be applied to swivel the first component relative to the second component is minimized and the moment of inertia barely changed. In the optimum arrangement, no additional torque is required and the moment of inertia is not changed.

However, it may also be advantageous if the drive shaft of the actuator does not extend parallel to the swivel axis. In this case, there is preferably a right angle between the direction of the drive shaft and the swivel axis.

Preferably, the actuator has a drive, for example in the form of a motor with a transmission. Both are preferably designed as one module and can be detached from each other. The transmission is preferably arranged on the first component or the second component. The motor is preferably arranged on the transmission. The modular design of motor and transmission means that a variety of combinations of motor and transmission can be provided with a limited choice of motors and/or transmissions to suit the individual needs of the patient.

The actuator preferably features an elastic element, particularly a spring, such as a torsion spring, and/or the actuator comprises a series elastic actuator and/or a parallel elastic actuator.

The transmission is preferably self-locking.

It is especially preferable if the actuator features a battery module that is preferably arranged on the motor or the transmission such that it can be detached. In a preferred configuration, the transmission is arranged on the first component or the second component, while the motor is arranged on the transmission and the battery module on the motor. This has the significant advantage that, for example, if the battery or rechargeable battery is empty, the battery module can be replaced easily and with little assembly effort by another battery module. It is advantageous if the battery module itself can be charged via a separate charging station, without it having to be in contact with the motor, the transmission or another component of the orthopedic joint to do so. If a wearer of a prosthesis that includes an orthopedic joint of the type described here has two battery modules, one of the battery modules can be charged while the other battery module supplies the motor with electrical energy. The motor is preferably an electric motor, such as a rotation motor.

In a preferred configuration, the actuator features a first coupling element, which interacts with a second coupling element that is arranged on the first component or the second component. This may be, for example, spur gearing, a magnetic coupling, peripheral toothing with claw coupling, or another type of coupling between the two coupling elements.

Preferably, the first coupling element is a driver, which can be brought into a first state and a second state. In the first state, it interacts with the second coupling element in such a way that the actuator swivels the first component relative to the second component in a first direction. To this end, the driver can, for example, rest on one side against the second coupling element of the first component or the second component. If the actuator is now actuated, the driver is rotated about the swivel axis, thereby also moving the second coupling element. Said coupling element is connected in a torque-proof manner to the one of the two components to which the actuator is not connected. If the actuator is connected to the first component, for example, the second coupling element is a coupling element of the second component and vice-versa. By rotating the driver about the swivel axis, the second coupling element is also moved about the swivel axis and a swivelling of the first component relative to the second component about the mutual swivel axis occurs.

In the second state of the driver, it preferably does not have an influence on a movement of the two components relative to one another. It is preferably not in contact with the second coupling element. In this sense, the orthopedic joint is thus a passive orthopedic joint, as the actuator is indeed present, but it is not configured to cause a swivelling of the two components relative to one another.

In an especially preferred configuration, the driver can also be brought into a third state in which it interacts with the second coupling element in such a way that the actuator swivels relative to the second component in a second direction. This second direction is preferably opposite to the first direction.

It is particularly preferable if the driver can also be designed in such a way that it can be arranged in a fourth state in which it can swivel the first component relative to the second component in both directions, depending on the direction in which the actuator is operated.

The various states into which the driver can be brought can be, for example, different positions and/or orientations of the driver relative to the component on which it is arranged.

An interface between the actuator and the first component or the second component is preferably waterproof. In this way, the orthopedic joint can also be used under water, for example when swimming, in the bath or in the shower.

The joint is preferably an orthotic joint, in particular an orthotic knee joint or an orthotic hip joint, or a prosthetic joint, in particular a prosthetic knee joint.

In a preferred configuration, the actuator can be brought into an active state and a passive state. In the active state, the actuator and especially its motor are configured to apply a force to the first and/or second component in order to swivel the first component relative to the second component in at least one direction. In the passive state, the actuator is not able to apply such a force. In this way, it is possible to conserve the energy supply of the actuator, for example a rechargeable battery for an electric motor, if the wearer of an orthopedic device containing the orthopedic joint does not need the support of the actuator, or at least not permanently.

The damping is preferably reduced when the actuator is brought into the active state. It is especially preferable if it is reduced as far as possible by the existing damper. For example, a throttle valve, which is arranged in a hydraulic damper, is opened as far as possible in order to reduce the damping as much as possible. In a preferred configuration, damping is reduced by bringing the actuator into the active state. This may be achieved, for example, by the actuating element that is actuated to bring the actuator into the active state also influencing the damping, for example by opening a hydraulic valve or pneumatic valve of the damper and thus reducing or removing a flow resistance.

The actuator can preferably be brought from the passive state into the active state and/or from the active state into the passive state by actuating an actuating element. The actuating element may be arranged, for example, directly on the orthopedic device, preferably on its actuator, especially preferably on its motor. It may be a switch, such as a toggle switch or a rotary switch, a button, a lever or another mechanical element. Alternatively or additionally, a tension element may be provided, for example in the form of a cable pull or a cable, that acts as an actuating element. If a tensile force is exerted on this tension element, the actuating element is actuated. Such cable pull systems are known, for example, for actuating hand prostheses. In this case, the cable pull that acts as an actuating element is often arranged on the untreated shoulder, so that the hand prosthesis can be opened or closed via the movement of this shoulder. Something similar is also possible with an orthopedic joint of the present type. If the orthopedic joint is arranged, for example, in an orthosis or prosthesis for the upper limb, the tension element can be arranged, for example, on the shoulder of the respective untreated limb.

As an alternative or in addition to these mechanic actuating elements, an electronic actuating element is preferably provided. For example, this may be an element represented on a display of the orthopedic joint, provided that this display is designed as a touchpad or touchscreen, for example. However, it is especially preferable if the electronic actuating element is not arranged directly on the orthopedic joint, but on an external device, for example. It is especially preferable if the actuating element is integrated into an app or a computer program product that is installed and executed on an external electronic data processing device, for example a PC, a laptop or in particular a smartphone. By actuating an actuating element, for example in the app of a smartphone, the actuator can be brought from the active to the passive state or vice versa. As such, the user of the orthopedic joint can decide on an individual basis whether they currently require the support of the actuator. If the drive is to be brought from the active state into the passive state or vice-versa, the user can do this automatically, quickly, easily and safely.

If the motor is in the active state, it has been proven to be advantageous if it does not permanently apply the force required to swivel the first component relative to the second component. If the orthopedic joint is a knee joint, for example, it may be beneficial to apply the support of the actuator needed for swivelling only in certain phases of a gait cycle, for example. This may be the swing phase, for example, in which the knee joint is stretched, i.e. extended, by the support of the actuator. The orthopedic joint therefore preferably features an electric control system, in particular an electronic data processing device, and at least one sensor which is configured to detect a variable that is relevant for a movement of the joint. This variable may be, for example, a joint angle of the orthopedic joint, a change in this joint angle, an acceleration or a torque path. Based on these measurement values and the sensor data generated from them in the sensor, the electronic control system can control the actuator. This is done depending on the sensor data of the at least one sensor. In this way, the energy available to the actuator, which is stored for example in an electrical energy storage device, for example a rechargeable battery, is used in such a way that the actuator can be used for as long as possible, i.e. for as many gait cycles as possible. A waste of energy can thus be avoided or at least reduced.

In a preferred configuration, the actuator can be operated in multiple modes in the active state. This configuration is based on the knowledge that, depending on the respective state of movement of the orthopedic device, which is equipped with the orthopedic joint of the type described here, different support modes are required or are advantageous. For example, the point in time within a gait cycle at which the drive should provide support depends on which movement the wearer of the orthopedic device is performing. For example, the at least one sensor can detect whether the wearer is walking along a level, along an incline or along a staircase. Different gait speeds can be determined. In addition, it is also possible, for example, to determine a weight borne by the wearer of the orthopedic device and the orthopedic joint. Depending on individual, several or all of these measurement data, the respective operating mode of the actuator can be configured by the electronic control system.

Alternatively or additionally, it is beneficial if the actuator can also be brought from one mode into another mode by actuating an actuating element. This actuating element can be the same actuating element by whose actuation the drive can also be brought from the passive state into the active state. Of course, it is also possible to provide different actuating elements.

The invention also solves the task by way of an orthopedic device, in particular an orthosis or prosthesis, with at least one orthopedic joint of the type described here.

BRIEF DESCRIPTION OF THE DRAWINGS

In the following, an example of an embodiment of the present invention will be explained in more detail by way of the attached figures: They show FIG. 1—the schematic representation of a joint according to a first example of an embodiment of the present invention, FIG. 2—the schematic representation of the coupling of the actuator in an exploded representation, and FIG. 3—a schematic representation of three different states of a coupling element.

DETAILED DESCRIPTION OF THE INVENTION

Figure 1:
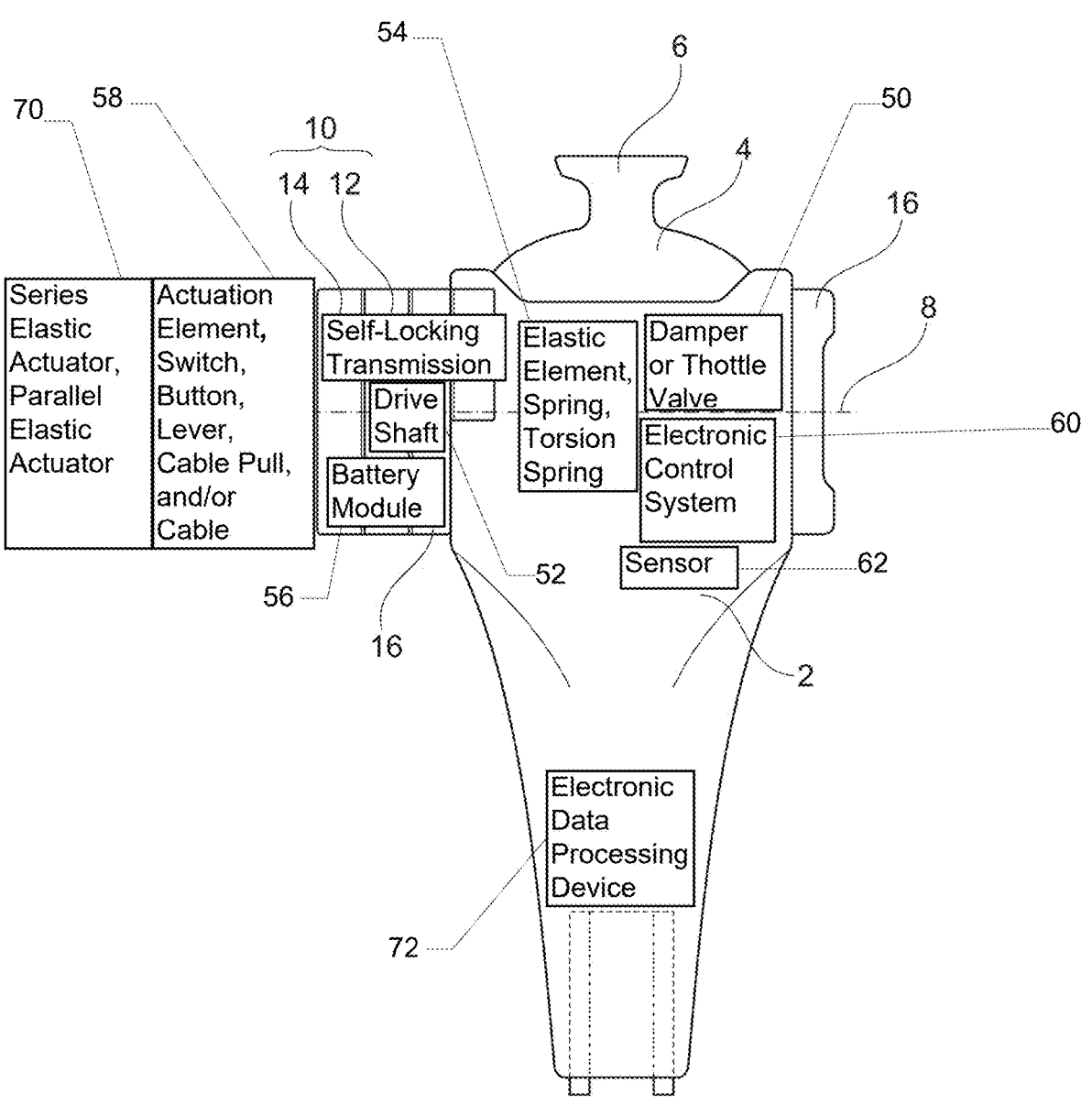

FIG. 1 shows an orthopedic joint in the form of an artificial knee joint comprising a first component 2 and a second component 4 arranged thereon. In the example of an embodiment shown, a lower leg element may be arranged at the lower end of the first component 2, while a pyramid adapter 6 is arranged at the upper end of the second component 4, wherein further prosthesis components, for example an upper leg socket, can be arranged on said pyramid adaptor.

The joint features a damper 50, an electronic control system 60, a sensor 62, and an electronic data processing device 72. The first component 2 is arranged relative to the second component 4 such that it can be swivelled about a swivel axis 8. The joint is an active joint that comprises an actuator 10 which features a self-locking transmission 12, a motor 14, a drive shaft 52, an elastic element, spring, or torsion spring 54, a battery module 56, an actuation element, switch, button, lever, cable pull, and/or cable 58, and a series elastic actuator and/or a parallel elastic actuator 70 in the example of an embodiment shown. The transmission is arranged on a fastening element 16 and is designed to be easily detachable. The motor 14 is arranged on the transmission 12 such that it can be easily detached, so that, for example, the motor 14 alone or in combination with the transmission 12 can be exchanged for another embodiment of transmission and motor, for example.

The joint is designed to be symmetrical. While in FIG. 1 a transmission 12 and a motor 14 are arranged on the left-hand side on the fastening element 16, the righthand side is also designed with a corresponding fastening element 16 without the components being arranged.

Figure 2:
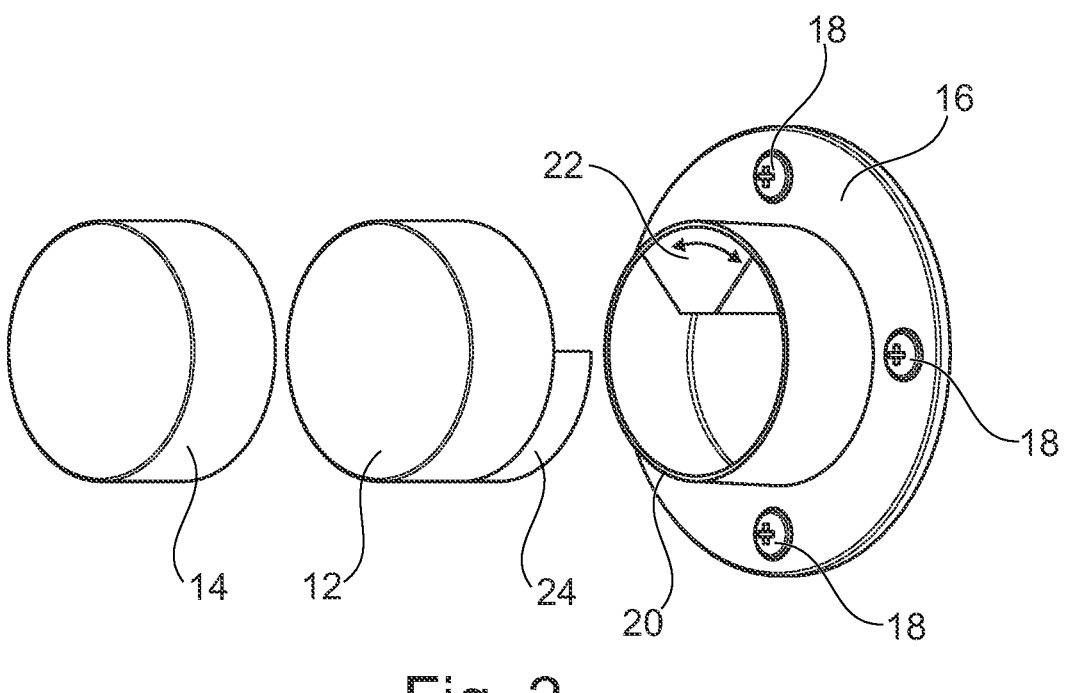

FIG. 2 depicts a section in an enlarged exploded representation. First, the fastening element 16 can be seen, which is arranged in a torque-proof manner on the first component 2 by means of screws 18. It has an annular projection 20 within which a second coupling element 22 is arranged, which is connected to the second component 4 such that it is torque-proof. On the transmission 12 there is a first coupling element 24 which, in the mounted state shown schematically in FIG. 1, projects into the annular projection 20. Depending on the position and orientation of the first coupling element 24 relative to the second coupling element 22, the various states of the coupling elements can be achieved.

Figure 3:
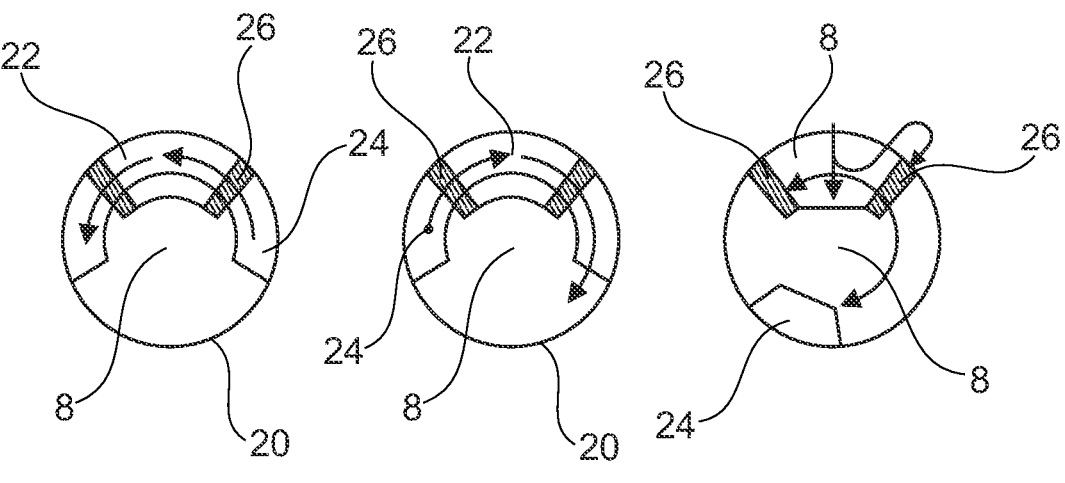

This is shown schematically in FIG. 3. A schematic view along the swivel axis 8 is shown in each case. The annular projection 20 can be seen, in which the second coupling element 22 is located in the upper area in each case. In the left-hand representation, the first coupling element 24 is shown to be resting on the second coupling element 22, separated by an elastic damping element 26. If the motor 14 or another actuator 10 is now driven so that the first coupling element 24, which is connected to the transmission 12 or another component of the actuator 10 in a torque-proof manner, moves in an anti-clockwise direction, the second coupling element 22 will also move and drive the joint. If the actuator 10 is driven in the opposite direction, so that the first coupling element 24 moves in the clockwise direction, there is no torque transmission so that the joint is not driven.

A different representation is depicted in the middle part of FIG. 3. Here too, the second coupling element 22 is located in the upper part within the annular projection 20. The first coupling element 24 is now situated to the left of the second coupling element 22, also separated from said element by an elastic damping element 26. The second coupling element 22 is now moved when the actuator 10 is operated in such a way that the first coupling element 24 moves in the clockwise direction.

In the right-hand representation of FIG. 3, the first coupling element 24 is in no contact at all with one of the elastic damping elements 26. Regardless of the direction in which the first coupling element 24 is moved by the actuator 10, there is no movement of the second coupling element 22 and thus no actuation of the joint.

REFERENCE LIST

2 first component
4 second component
6 pyramid adapter
8 swivel axis
10 actuator
12 transmission
14 motor
16 fastening element
18 screw
20 projection
22 second coupling element
24 first coupling element
26 elastic damping element

We claim:
1. An orthopedic joint comprising:
a first component,
a second component that is arranged on the first component such that it can be swiveled about a swivel axis,
an actuator for swiveling the first component relative to the second component in at least one direction, wherein the actuator comprises a first coupling element which interacts with a second coupling element arranged on either the first component or the second component, wherein the actuator further comprises a motor module and a transmission module, the motor module and the transmission module being detachable from each other; and
at least one damper configured to adjustably dampen a swiveling of the first component relative to the second component during the swiveling of the first component relative to the second component, and wherein the at least one damper comprises a throttle valve;
wherein the actuator is arranged on the first component or the second component on a medial or lateral side such that it can be detached, wherein, when the actuator is arranged on the medial side of the first component or the second component, the transmission module is connected to the medial side of the first component or the second component and the motor module is connected to a medial side of the transmission module, and wherein, when the actuator is arranged on the lateral side of the first component or the second component, the transmission module is connected to the lateral side of the first component or the second component and the motor module is connected to a lateral side of the transmission module, wherein the first coupling element comprises a driver which can be brought into a first state, a second state, or a third state, wherein, in the first state, the first coupling element interacts with the second coupling element in such a way that the actuator swivels the first component relative to the second component in a first direction and driving the actuator in a second direction does not swivel the first component or the second component relative to each other, wherein, in the second state, the first coupling element does not interact with the second coupling element, and wherein, in the third state, the first coupling element interacts with the second coupling element in such a way that the actuator swivels the first component relative to the second component in the second direction and driving the actuator in the first direction does not swivel the first component or the second component relative to each other.

2. The orthopedic joint of claim 1 characterized in that a drive shaft of the actuator extends parallel to the swivel axis.

3. The orthopedic joint of claim 1, characterized in that the actuator features an elastic element, a torsion spring, and/or a series elastic actuator and/or a parallel elastic actuator.

4. The orthopedic joint of claim 1, characterized in that the transmission module is self-locking.

5. The orthopedic joint of claim 1, characterized in that the actuator comprises a battery module which is arranged on the motor module or transmission module such that it can be detached.

6. The orthopedic joint of claim 1, characterized in that an interface between the actuator and the first component or the second component is waterproof.

7. The orthopedic joint of claim 1, characterized in that the joint is an orthotic joint comprising an orthotic knee joint or an orthotic hip joint, or a prosthesis joint comprising a prosthetic knee joint.

8. The orthopedic joint of claim 1, characterized in that the actuator can be brought into an active state and a passive state, wherein the damping is reduced when the actuator is brought into the active state.

9. The orthopedic joint of claim 8, characterized in that the actuator can be brought from the passive state into the active state and/or vice versa by actuating an actuating element, wherein the actuating element comprises at least one of a switch, button or lever, a cable pull, or cable arranged on the joint, on the actuator, or an electronic actuating element, wherein the electronic actuating element comprises an app on an electronic data processing device.

10. The orthopedic joint of claim 8, characterized in that the joint has an electronic control system comprising an electronic data processing device, and at least one sensor which is set up to detect a variable relevant to a movement of the joint, and the electronic control system is configured to control the actuator depending on the sensor data of the at least one sensor.

11. An orthopedic device with at least one orthopedic joint according to claim 1.

12. An orthopedic joint comprising:
a first component;
a second component that is arranged on the first component such that it can be swiveled about a swivel axis;
at least one damper configured to adjustably dampen a swiveling of the first component relative to the second component during the swiveling of the first component relative to the second component, and wherein the at least one damper comprises a throttle valve; and
an actuator for swiveling the first component relative to the second component in at least one direction, wherein the actuator comprises a first coupling element which interacts with a second coupling element arranged on either the first component or the second component, wherein the actuator further comprises a motor module and a transmission module, the motor module and the transmission module being detachable from each other;
wherein the actuator is arranged on the first component or the second component on a medial or lateral side such that it can be detached, wherein, when the actuator is arranged on the medial side of the first component or the second component, the transmission module is connected to the medial side of the first component or the second component and the motor module is connected to a medial side of the transmission module, and wherein, when the actuator is arranged on the lateral side of the first component or the second component, the transmission module is connected to the lateral side of the first component or the second component and the motor module is connected to a lateral side of the transmission module, wherein the first coupling element comprises a driver which can be brought into a first state, a second state, or a third state, wherein, in the first state, the first coupling element interacts with the second coupling element in such a way that the actuator swivels the first component relative to the second component in a first direction and driving the actuator in a second direction does not swivel the first component or the second component relative to each other, wherein, in the second state, the first coupling element does not interact with the second coupling element, and wherein, in the third state, the first coupling element interacts with the second coupling element in such a way that the actuator swivels the first component relative to the second component in the second direction and driving the actuator in the first direction does not swivel the first component or the second component relative to each other.

13. An orthopedic joint comprising:
a first component;
a second component that is arranged on the first component such that it can be swiveled about a swivel axis;
at least one damper configured to adjustably dampen a swiveling of the first component relative to the second component during the swiveling of the first component relative to the second component, and wherein the at least one damper comprises a throttle valve; and
an actuator with a motor module, a transmission module and an elastic element for swiveling the first component relative to the second component in at least one direction, wherein the actuator comprises a first coupling element which interacts with a second coupling element arranged on either the first component or the second component, wherein the motor module and the transmission module being detachable from each other;
wherein the actuator is arranged on the first component or the second component on a medial or lateral side such that it can be detached, wherein, when the actuator is arranged on the medial side of the first component or the second component, the transmission module is connected to the medial side of the first component or the second component and the motor module is connected to a medial side of the transmission module, and wherein, when the actuator is arranged on the lateral side of the first component or the second component, the transmission module is connected to the lateral side of the first component or the second component and the motor module is connected to a lateral side of the transmission module, wherein the first coupling element comprises a driver which can be brought into a first state, a second state, or a third state, wherein, in the first state, the first coupling element interacts with the second coupling element in such a way that the actuator swivels the first component relative to the second component in a first direction and driving the actuator in a second direction does not swivel the first component or the second component relative to each other, wherein, in the second state, the first coupling element does not interact with the second coupling element, and wherein, in the third state, the first coupling element interacts with the second coupling element in such a way that the actuator swivels the first component relative to the second component in the second direction and driving the actuator in the first direction does not swivel the first component or the second component relative to each other.

\* \* \* \* \*